United States Patent [19]

Miyagawa et al.

[11] Patent Number: 4,701,413

[45] Date of Patent: Oct. 20, 1987

[54] METHOD OF PRODUCING INOSINE AND/OR GUANOSINE

[75] Inventors: Kenichiro Miyagawa, Ibaraki; Muneharu Doi, Takarazuka; Shun-ichi Akiyama, Fujisawa, all of Japan

[73] Assignee: Takeda Chemical Industries, Ltd., Osaka, Japan

[21] Appl. No.: 515,260

[22] Filed: Jul. 19, 1983

[30] Foreign Application Priority Data

Jul. 27, 1982 [JP] Japan .................................. 57-131664

[51] Int. Cl.⁴ ...................... C12P 19/40; C12N 15/00; C12N 1/20; C12R 1/07; C12R 1/125
[52] U.S. Cl. ................................... 435/88; 435/172.1; 435/253; 435/832; 435/839
[58] Field of Search ........................ 435/87, 88, 91, 92, 435/243, 244, 253, 813, 832, 839, 172.1

[56] References Cited

U.S. PATENT DOCUMENTS

| | | | |
|---|---|---|---|
| 3,298,923 | 1/1967 | Banno et al. | 435/88 |
| 3,912,587 | 10/1973 | Enei et al. | |
| 3,960,660 | 6/1976 | Enei et al. | |
| 3,960,661 | 6/1976 | Enei et al. | 435/88 |
| 3,969,188 | 7/1976 | Enei et al. | |

FOREIGN PATENT DOCUMENTS 5162998  12/1980  Japan .................................. 435/88

OTHER PUBLICATIONS

Lehninger, A., in *Biochemistry* 2d edition, Worth Publishers, Inc., pp. 345–347 & 729–735.
Kornberg (1980), DNA Replication, W. H. Freeman and Company, p. 422.
Kornberg (1982), 1982 Supplement to DNA Replication, W. H. Freeman and Company, p. S133.
Anand (1975), Antibiotics, vol. III, ed–Corcoran & Hahn, pp. 668–678.

*Primary Examiner*—Esther M. Kepplinger
*Attorney, Agent, or Firm*—Wenderoth, Lind & Ponack

[57]  ABSTRACT

Method of producing inosine and/or guanosine by culturing an inosine and/or guanosine-producing mutant of the genus Bacillus which requires adenine for growth and is resistant to an antifolate. Thus, inosine and/or guanosine can be produced in much greater yields, compared with known methods.

10 Claims, No Drawings

METHOD OF PRODUCING INOSINE AND/OR GUANOSINE

This invention relates to a method of producing inosine and/or guanosine.

Inosine and guanosine are important starting materials for the synthetic production of condiments, namely 5'-inosinic acid and 5'-guanylic acid, and it is of great commercial significance to produce them in large quantities. For the production of inosine and/or guanosine by way of fermentation, it has been considered advantageous from industrial views to employ a mutant strain in which one or more of such properties as adenine/adenosine resistance, GMP reductase deficiency, and nucleotide phosphorylase deficiency have been constructed.

The intensive research undertaken by the present inventors for the purpose of improving the conventional fermentative production of inosine and/or guanosine led to the finding that the accumulation of inosine and/or guanosine by an inosine and/or guanosine producing microorganism of the genus Bacillus requiring adenine for growth can be remarkably increased by causing the microorganism to acquire resistance to antifolates such as methotrexate, aminopterin, pyrimethamine, trimethoprim, etc.

This invention is therefore concerned with a method of producing inosine and/or guanosine, which comprises culturing a mutant strain of the genus Bacillus which requires adenine for growth and is resistant to antifolates and capable of producing inosine and/or guanosine is cultivated in a medium and the inosine and/or quanosine elaborated and accumulated thereby is recovered from the resulting culture broth.

The microorganism employed in accordance with this invention is an inosine and/or guanosine producing strain of the genus Bacillus which requires adenine for growth and has resistance to antifolates.

The antifolates (folic acid antagonistics) used in this invention are the drugs which show antagonistically inhibitory action to dihydrofolate reductase or to one carbon transfer reactions in which folic acid participates.

As such antifolates, there may be mentioned methotrexate, aminopterin, trimethoprim or pyrimethamine, etc.

The mutants used in the present invention can be derived from a broad range of parents including not only the wild strains of *Bacillus pumilus, Bacillus subtilis, Bacillus licheniformis*, etc. but also inosine and/or quanosine-producing strains of the genus Bacillus [e.g. *Bacillus pumilus* No. 158-A-11 (IFO 12476) described in Japanese Patent Publication No. 46839/1976.] Adenine-requiring mutants are obtained by the replica plating technique.

The derivation abd isolation of the microorganism for use in accordance with this invention can be easily accomplished by the established procedures. Thus, the desired mutant strain can be obtained by subjecting a microorganism of the genus Bacillus, e.g. *Bacillus pumilus, Bacillus subtilis, Bacillus licheniformis*, to a conventional treatment, such as ultraviolet irradiation, N-methyl-N'-nitro-N-nitrosoguanidine (NTG) treatment, etc., then cultivating the treated microorganism on a plate medium containing an antifolate in a concentration which does not permit growth of the parent strain, and selecting the resulting colony.

In the above plate medium, the concentration of antifolate varies with, among others, kinds of parent microorganisms or medium composition. For example, in case the below-mentioned medium (A) containing agar is employed, methotrexate, aminopterin, trimethoprim or pyrimethamine is added thereto in a concentration as follows:

methotrexate: more than 10 $\mu$g/ml, preferably more than 50 $\mu$g/ml, aminopterin: more than 20 $\mu$g/ml, preferably more than 100 $\mu$g/ml, trimethoprim: more than 0.2 $\mu$g/ml, preferably more than 10 $\mu$g/ml, pyrimethamine: more than 10 $\mu$g/ml, preferably more than 50 $\mu$g/ml.

The degree of resistance of the derived mutant to antifolates can be evaluated by the following procedure. A test tube containing 5 ml of a medium (B) prepared by adding an antifolate in a predetermined concentration to the medium (A) shown in Table 1 is inoculated with about $10^6$ cells/ml of the test strain previously grown on a nutrient agar (Difco) slant and shake culture is conducted at 37° C. for 24 hours. The resulting broth is diluted 10-fold with water and the absorbance of the dilution at 590 nm is measured to find the degree of growth (B590). With the degree of growth (A590) of the same strain on the folic acid-free medium (A) being taken as 100, the relative growth on such an antifolate-containing medium can be expressed by (B590/A590)×100.

TABLE 1

| Composition of Medium | Concentration |
| --- | --- |
| Glucose | 5.0% |
| Ammonium sulfate | 0.3% |
| Sodium glutamate | 1.0% |
| α-Alanine | 0.5% |
| Magnesium sulfate | 0.01% |
| Dipotassium hydrogen phosphate | 0.1% |
| Manganese sulfate | 2 mg/l |
| Zinc sulfate | 2 mg/l |
| Biotin | 100 $\mu$g/l |
| Thiamine | 100 $\mu$g/l |
| Adenosine | 200 $\mu$g/l |
| Histidine | 200 $\mu$g/l |

The term "resistant strain" as used in this specification means any mutant strain that gives a relative degree of growth in excess of that of the parent strain in an antifolate-containing medium. As examples of the mutants that can be employed in the practice of this invention, there may be mentioned *Bacillus pumilus* NA-1101 (IFO 14184, FERM P-6639), *Bacillus pumilus* NA-1102 (IFO 14185, FERM P-6640), *Bacillus pumilus* NA-1103 (IFO 14186, FERM P-6641), *Bacillus subtilis* NA-6011 (IFO 14189, FERM P-6642) and *Bacillus subtilis* NA-6012 (IFO 14190, FERM P-6643).

The above IFO numbers are the deposit numbers assigned to the strains by the Institute for Fermentation, Osaka (IFO), 17-85, Juso-honmachi 2-chrome, Yodogawa-ku, Osaka, Japan. Type cultures of the above-identified microorganisms have been deposited with IFO since July 13, 1982.

Sub-cultures of these microorganisms, which were deposited on July 22, 1982 at Fermentation Research Institute, Agency of Industrial Science and Technology, Ministry of International Trade and Industry, Japan (FRI) under the accession numbers of FERM P as shown above, the deposit being converted to a deposit under the Budapest Treaty, have been stored at FRI under the accession numbers of FERM BP as follows:

| Strain | The Accession Numbers under the Budapest Treaty |
|---|---|
| *Bacillus pumilus* NA-1101 | FERM BP-288 |
| *Bacillus pumilus* NA-1102 | FERM BP-289 |
| *Bacillus pumilus* NA-1103 | FERM BP-290 |
| *Bacillus subtilis* NA-6011 | FERM BP-291 |
| *Bacillus subtilis* NA-6012 | FERM BP-292 |

The above-mentioned NA-1101, NA-1102 and NA-1103 strains were derived from *Bacillus pumilus* No. 158-A-11 strain (IFO 12476) as parent strain, and NA-6011 and NA-6012 strains from *Bacillus subtilis* No. 115 (IFO 14187) as the parent strain.

Microbiological characteristics of these mutant strains are similar to those of the respective parent strains.

Microbiological characteristics of the respective parent strains are as follows:

|  | *Bacillus pumilus* No. 158-A-11 (IFO 12476) | *Bacillus subtilis* No. 115 (IFO 14187) |
|---|---|---|
| a. Morphology | | |
| (1) Shape and size | Rods 0.6 × 3 μ | Rods 0.3 × 3 μ |
| (2) Polymorphism | Singly or rarely in chains | Singly or rarely in pairs |
| (3) Motility | Non-motile | Non-motile |
| (4) Sporulation | Yes | Yes |
| Shape of spore | Ellipsoidal | Ellipsoidal |
| Swelling sporangium | No | No |
| Position of spore | Central or para-central | Central or para-central |
| (5) Gram's stain | Positive | Positive |
| (6) Acid fastness | Negative | Negative |
| b. Cultural characteristics | | |
| (1) Bouillon agar plate | Round or undulated, convex, lenticular, opaque and white to pale yellow. | Amorphous and diffused, rough surface, flat, opaque and white to light brown. |
| (2) Bouillon agar slant | Convex to raised, opaque and white to pale yellow. | Flat, opaque and white to light brown. |
| (3) Bouillon liquid | Coherent pellicle, no turbidity, rarely no surface growth with some turbidity. | Coherent pallicle, no turbidity. |
| (4) Litmus milk | Alkaline, peptonization, reduction | Alkaline, peptonization, reduction |
| c. Physiological characteristics | | |
| (1) Reduction of nitrates | Negative | Positive |
| (2) V-P reaction | Positive | Positive |
| (3) Hydrolysis of starch | Negative | Positive |
| (4) Utilization of citrate | Positive | Positive |
| (5) Utilization of propionate | Negative | Negative |
| (6) Utilization of ammonium salts | Positive | Positive |
| (7) Urease | Weakly positive | Weakly positive |
| (8) Catalase | Positive | Positive |
| (9) Oxygen requirement | Aerobic, no growth under anaerobic conditions | Aerobic, no growth under anaerobic conditions |
| (10) Growth in 7% sodium chloride | Positive | Positive |
| (11) Growth in media, pH 5.7 | Positive | Positive |
| (12) Biotin requirement | Positive | Negative |

Comparison of the above characteristics of IFO 12476 and IFO 14187 strains with the comparable descriptions in Bergey's Manual of Determinative Bacteriology, R. E. Buchanan and N. E. Gibbons (ed.), Edition 8, 1974 showed that they belong to *Bacillus pumilus* and *Bacillus subtilis*.

The medium used for cultivating such an inosine and/or guanosine-producing strain for the production of inosine and/or guanosine may be any of the media commonly employed for inosine and/or guanosine fermentation. Regarding the composition of the medium, the carbon sources may be sugars such as glucose, maltose, starch hydrolysate, etc., monohydric or polyhydric alcohols such as glycerin, ethanol, sorbitol, etc., and fatty acids such as acetic acid, propionic acid, stearic acid, oleic acid, etc., and these carbon sources are used either singly or in combination. The nitrogen sources include, among others, organic nitrogen sources such as peptone, soybean meal, corn steep liquor, yeast, meat extract, urea, etc., ammonium salts of sulfuric acid, nitric acid, hydrochloric acid, carbonic acid, etc., and inorganic nitrogen sources such as gaseous ammonia, aqueous ammonia, etc., and these nitrogen sources may be used singly or in combination. As other nutrient sources, there may be employed various inorganic salts necessary for growth of the strain, such as the sulfates, hydrochlorides, carbonates, nitrates, phosphates, acetates, etc. of calcium, potassium, sodium, magnesium, manganese, iron, copper, zinc, etc. as well as the amino acids, vitamins, etc. necessary for growth of the organism. These nutrient sources may be used singly or in combination. As sources of adenine, there may be employed not only adenine, adenosine, adenylic acid, ribonucleic acid, etc. but also natural materials such as microbial cells containing them, extracts thereof, meat extract, etc. Moreover, defoaming agents and surfactants such as silicone oil, polyalkylene glycol ether, etc. may also be incorporated in the medium as necessary.

Cultivation is generally conducted under aerobic conditions, for example by shake culture or by aerated submerged culture. The medium is preferably maintained within the range of pH 4 to pH 9. If there is a fluctuation of pH in the course of fermentation, it may be corrected by adding an aqueous solution or suspension of alkali hydroxide, calcium carbonate, ammonia or the like or ammonia gas from time to time. The cultivation temperature is generally within the range of from 20° to 45° C. and the optimum temperature for growth of the microorganism and for accumulation of inosine and/or guanosine is selected. Cultivation is continued until the accumulation of inosine and/or guanosine reaches a maximal level and it is generally sufficient to carry out fermentation for 24 to 144 hours.

Separation and recovery of inosine and/or guanosine from the fermenation broth can be effected by the conventional method, e.g. precipitation, ion exchange resin or activated carbon chromatography, etc.

According to the present invention, inosine and/or guanosine can be produced in much greater yields, compared with known methods.

The following examples are intended to illustrate this invention in further detail.

EXAMPLE 1

*Bacillus pumilus* No. 158-A-11 (IFO 12476) [hereditary characteristics: adenine requiring, adenine/guanosine-resistant, guanylic acid reductase-deficient, and histidine-requiring] was treated with nitrosoguanidine (NTG) in the conventional manner and then streaked on a plate prepared by adding 50 μg/ml of methotrexate and 25 g/l of agar to the medium A of Table 1. The inoculated medium was incubated at 37° C. for 3 days and *Bacillus pumilus* NA-1101 (IFO 14184, FERM BP-288) was selected from among the colonies. The resistance to methotrexate (relative growth) of this strain as well as that of the parent strain was determined by the method hereinbefore described. The results are shown in Table 2.

TABLE 2

| Strain | Relative growth Methotrexate added (μg/ml) | | | | | |
|---|---|---|---|---|---|---|
| | 0 | 1 | 2 | 4 | 8 | 15 |
| NA-1101 | 100 | 100 | 100 | 100 | 100 | 88 |
| No. 158-A-11 | 100 | 80 | 65 | 43 | 40 | 18 |

Then, a 200 ml conical flask containing 20 ml of the seed culture medium of Table 3 was inoculated with a loopful of *Bacilus pumilus* NA-1101 grown on a nutrient agar (Difco) plate and shake culture was conducted at 37° C. for 18 hours. A portion (1 ml) of the culture was transferred to a 200 ml creased flask containing 20 ml of the main fermentation medium indicated in Table 3, and cultivation was conducted on a rotary shaker at 37° C. for 4 days. The yield of guanosine was 23.0 mg/ml.

TABLE 3

| Seed culture | | Main fermentation medium | |
|---|---|---|---|
| Composition of medium | Concentration | Composition of medium | Concentration |
| Sorbitol | 2.0% | Glucose | 15.0% |
| Dried yeast | 1.5% | Ammonium sulfate | 2.0% |
| Potassium dihydrogen phosphate | 0.1% | Urea | 1.0% |
| | | Sodium glutanate | 1.0% |
| | | Corn steep liquor | 2.0% |
| Dipotassium hydrogen phosphate | 0.3 | Crude nucleic acid | 0.2% |
| | | Calcium chloride | 0.59 |
| | | Magnesium sulfate | 0.2 |
| Histidine | 0.01% | Potassium chloride | 0.05% |
| | | Calcium carbonate | 3.0% |
| | | Biotin | 200 μg/l |
| | | Manganese sulfate | 2.5 mg/l |

The above procedure was carried out for a total of about 50 flasks to obtain 1 liter of broth. This broth was adjusted to pH 11 with sodium hydroxide to dissolve the guanosine crystals and, then, centrifuged to remove the cells. The resulting supernatant was neutralized and cooled to give 21.0 g of crude crystals of guanosine. These crystals were dissolved in 900 ml of hot water, decolorized with activated carbon, and allowed to stand in the cold to precipitate the quanosine. 18.4 g of pure crystals of quanosine was obtained. Cultivation of the parent No. 158-A-11 strain under the same conditions resulted in the accumulation of guanosine only in a yield of 4.5 mg/ml.

EXAMPLE 2

*Bacillus pumilus* No. 158-A-11 was subjected to ultraviolet irradiation and NTG treatment in the conventional manner and, as described in Example 1, streak-cultured on the plate medium prepared by adding 200 μg/ml of amino-pterin and 25 g/l of agar to the medium A, followed by selection of a colony of *Bacillus pumilus* NA-1102 (IFO 14185, FERM BP-289). This strain was cultivated under the same conditions as Example 1. The yields of inosine and quanosine in the broth were 18 mg/ml and 6 mg/ml, respectively.

EXAMPLE 3

*Bacillus subtilis* No. 115 (wild strain) (IFO 14187) was subjected to the conventional NTG treatment and the replica plating technique to obtain an adenine-requiring mutant NA-6001 (IFO 14188).

This strain was further treated with NTG three times to obtain *Bacillus subtilis* NA-6011 (IFO 14189, FERM BP-291), a strain which can grow on the plate medium prepared by adding 100 μg/ml of aminopterin and 25 g/l of agar to the medium A. The aminopterin-resistance and inosine/quanosine producing ability of each of these strains were determind by the procedures described in Example 1. The results are shown in Table 4 and Table 5, respectively.

TABLE 4

| Strain | Relative growth Aminopterin added (μ/ml) | | | | | |
|---|---|---|---|---|---|---|
| | 0 | 4 | 8 | 15 | 30 | 60 |
| NA-6011 | 100 | 100 | 97 | 95 | 89 | 52 |
| NA-6001 | 100 | 85 | 75 | 55 | 22 | 13 |

TABLE 5

| Strain | Accumulation of inosine | Accumulation of quanosine |
|---|---|---|
| NA-6011 | 18 mg/ml | 5 mg/ml |
| NA-6001 | 1 | — |

EXAMPLE 4

*Bacillus pumilus* No. 158-A-11 was subjected to the conventional NTG treatment to give *Bacillus pumilus* NA-1103 (IFO 14186, FERM BP-290), a mutant strain capable of growing on the plate medium prepared by adding 10 μg/ml of trimethoprim and 25 g/l of agar to the medium A. The trimethoprim resistance of this strain is shown in Table 6.

TABLE 6

| Strain | Relative growth Trimethoprim added (g/ml) | | | | |
|---|---|---|---|---|---|
| | 0 | 0.1 | 0.25 | 0.5 | 1.0 |
| NA-1103 | 100 | 100 | 100 | 100 | 89 |
| NA-158-A-11 | 100 | 36 | 17 | 10 | 7 |

When this strain was cultivated under the same conditions as Example 1, guanosine was accumulated at the rate of 22 mg/ml.

EXAMPLE 5

*Bacillus subtilis* NA-6001 (IFO 14188) was treated with NTG four times to obtain *Bacillus subtilis* NA 6012 (IFO 14190, FERM BP-292), a mutant strain capable of growing on the plate medium prepared by adding 50

μg/ml of pyrimethamine and 25 g/l of agar to the medium A. The pyrimethamine resistance of this mutant is shown in Table 7.

TABLE 7

| Strain | Relative growth Pyrimethamine (μg/ml) | | | | | | | |
|---|---|---|---|---|---|---|---|---|
| | 0 | 0.5 | 1.5 | 3.0 | 6.0 | 12 | 25 | 50 |
| NA-6012 | 100 | 100 | 86 | 76 | 66 | 52 | 49 | 26 |
| NA-6001 | 100 | 85 | 56 | 26 | 6 | 2 | 2 | 2 |

When this mutant was cultivated under the conditions as Example 1, inosine and guanosine were accumulated at the rates of 9 mg/ml and 14 mg/ml, respectively.

What we claim is:

1. A method of producing inosine and/or guanosine, which comprises culturing a mutant strain of the genus Bacillus, which requires adenine for growth and is resistant to an antifolate selected from the group consisting of methotrexate, aminopterin, pyrimethamine and trimethoprim and capable of producing inosine and/or guanosine, in a medium to cause the strain to elaborate and accumulate inosine and/or guanosine in culture broth and the inosine and/or guanosine so accumulated are recovered from said broth.

2. The method according to claim 1, wherein the said antifolate is methotrexate.

3. The method according to claim 1, wherein the said antifolate is aminopterin.

4. The method according to claim 1, wherein the said antifolate is pyrimethamine.

5. The method according to claim 1, wherein the said antifolate is trimethoprim.

6. The method according to claim 1, wherein the mutant is of the species *Bacillus pumilus*.

7. The method according to claim 1, wherein the mutant is of the species *Bacillus subtilis*.

8. The method according to claim 1, wherein the mutant is *Bacillus pumilus* NA-1101 (FERM BP-288), *Bacillus pumilus* NA-1102 (FERM BP-289) or *Bacillus pumilus* NA-1103 (FERM BP-290).

9. The method according to claim 1, wherein the mutant is *Bacillus subtilis* NA-6011 (FERM BP-291) or *Bacillus subtilis* NA-6012 (FERM BP-292).

10. A biologically pure culture of the microorganism belonging to the genus Bacillus having the characteristics identifiable with those of FERM BP-288, FERM BP-289, FERM BP-290, FERM BP-291 or FERM BP-292, said culture being capable of producing, in a culture medium containing assimilable carbon and digestible nitrogen sources, a recoverable amount of inosine and/or guanosine.

* * * * *